United States Patent
Maffei et al.

(10) Patent No.: US 8,748,449 B2
(45) Date of Patent: *Jun. 10, 2014

(54) USE OF POLYOLS TO OBTAIN STABLE POLYMORPHOUS FORMS OF RIFAXIMIN

(75) Inventors: Paola Maffei, Bologna (IT); Milena Bachetti, Bologna (IT); Giuseppe Bottoni, Bologna (IT); Giuseppe Claudio Viscomi, Bologna (IT)

(73) Assignee: Alfa Wassermann S.p.A., Alanno (PE) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,945

(22) Filed: Jul. 9, 2012

(65) Prior Publication Data

US 2013/0072676 A1    Mar. 21, 2013

Related U.S. Application Data

(62) Division of application No. 12/439,094, filed as application No. PCT/IB2007/002199 on Jul. 31, 2007, now Pat. No. 8,217,054.

(30) Foreign Application Priority Data

Sep. 5, 2006  (IT) ............................... MI2006A1692

(51) Int. Cl.
  *A61K 31/44*   (2006.01)
  *A61K 31/437*  (2006.01)

(52) U.S. Cl.
  CPC .................................. *A61K 31/437* (2013.01)
  USPC ....................................................... 514/283

(58) Field of Classification Search
  CPC .................................................... A61K 31/437
  USPC ....................................................... 514/283
  See application file for complete search history.

(56) References Cited

U.S. PATENT DOCUMENTS 8,217,054 B2 *   7/2012 Maffei et al. ................. 514/283
2005/0272754 A1  12/2005 Viscomi et al.

FOREIGN PATENT DOCUMENTS

EP         1676847        7/2006
WO     WO 2006/094737     9/2006

OTHER PUBLICATIONS

Arthur H. Kibbe, "Handbook of Pharmaceutical Excipients," 2000, American Pharmaceutical Association and Pharmaceutical Press, p. 165.
Arthur H. Kibbe, "Handbook of Pharmaceutical Excipients," 2000, American Pharmaceutical Association and Pharmaceutical Press, p. 442.
Quing Li, et al., "Solvothermal growth of vaterite in the presence of ethylene glycol, 1,2-propanediol, and glycerine," Journal of Crystal Growth, 236 (2002) 357-362.
R.M. Uresti, et al., "Effects of sugars and polyols on the function and mechanical properties of pressure-treated arrowtooth flounder (*Atheresthes stomias*) proteins," Food Hydrocolloids, 19 (2005) 964-973.
Vippagunta et al. solids, Advanced Drug Delivery Reviews, May 2001,48(1), 3-26.

* cited by examiner

*Primary Examiner* — Paul Zarek
(74) *Attorney, Agent, or Firm* — Steinfl & Bruno LLP (57) ABSTRACT

Polyols stabilize polymorphous form of rifaximin, in particular the β form. When polyols having at least two hydroxy groups are added to rifaximin powder, polymorph β is stable and remains stable in time independently from the environment humidity.
In this invention a method to prepare formulations constituted by pure and stable polymorphous forms able to give a pharmaceutical product is described.

36 Claims, 5 Drawing Sheets

USE OF POLYOLS TO OBTAIN STABLE POLYMORPHOUS FORMS OF RIFAXIMIN

RELATED APPLICATIONS

This application is a divisional of U.S. patent application Ser. No. 12/439,094, filed Feb. 26, 2009, now U.S. Pat. No. 8,217,054, which is a national stage application under 35 U.S.C. §371 of International Application PCT/IB2007/002199, filed Jul. 31, 2007, which claims priority to Italian Application No. MI2006A001692, filed Sep. 5, 2006, the contents of each of which are incorporated herein in their entirety.

BACKGROUND OF THE INVENTION

The active ingredients, contained in medicinal products, can be available in polymorphous forms having different chemical-physical properties, as for example solubility and chemical stability.

For medicinal products both these properties are critical for the in vivo absorption of the active ingredient, and consequently, for the efficacy and safety of the product after administration in humans or animals.

A large number of scientific papers is available on this topic. Some articles are for example: doxazosin (Sohn Y. T. et al., Arch. Pharm. Res., 2005; 28, 730-735); tranilast (Vogt F. G. et al., J. Pharm. Sci., 2005, 94, 651-65); clopidogrel (Koradia V., et al., Acta. Pharm., 2004, 54 (3), 193-204); celecoxib (Chawla G. et al., Pharm. Dev. Technol., 2004, 9 (4), 419-33); ketorolac (Sohn Y. T. et al., Arch. Pharm. Res. 2004, 27 (3), 357-60); fluconazol (Caira M. R. et al., J. Pharm. Sci., 2004, 93 (3), 601-11); piroxicam (Vrecer F. et al., Int. J. Pharm., 2003, 256 (1-2), 3-15); theophylline (Airaksinen S. et al., Int. J. Pharm., 2004, 276 (1-2), 129-41).

For the above mentioned reasons the medical authority responsible for the approval of the marketing of medicinal products requires information on the properties and the production consistency of the polymorphous active ingredients in the solid state; it is important to avoid modification of the polymorphous form during the production stage and storage of the pharmaceutical preparation. For this purpose, it is important to select from among all the possible polymorphous forms those showing the highest stability in time, as described by Rodriguez-Spong B. et al. in Adv. Drug Deliv. Rev., 2004, 56 (3), 241-74.

To obtain a more stable polymorphous form, saline active ingredients are often used, as described in Adv. Drug Del. Rev., 2006, 56, 231-334.

Rifaximin is an antibiotic belonging to the rifampicin family, available in tablets, granules for oral suspension and ointment, marketed in Europe, in the U.S.A. and in many other countries.

Rifaximin can exist in the polymorphous forms α, β and γ described by Viscomi G. C. et al. in IT MI2003 A 002144, (2003) and U.S. Pat. No. 7,045,620 B1, (2003), and in the polymorphous forms δ and ε described by Viscomi G. C. et al. in EP 1698630 (2005). These polymorphous forms are very important because they can change the intrinsic dissolution by approximately ten times and the bioavailability of rifaximin by almost six hundred times, as described by Viscomi et al. in WO 2005/044823 (2004). These changes can have a strong effect on the efficacy and the safety of the product.

Moreover it is known from U.S. Pat. No. 7,045,620 B1, (2003) and EP 1698630 (2005) that the rifaximin polymorphous forms can easily convert into other forms depending on the possibility to acquire or to lose water. These transformations can occur also in the solid state, because of changes in humidity and temperature conditions. For example in environments with a relative humidity around 50% or higher, polymorph α converts into polymorph β. Another example is represented by polymorph ε, that can be obtained by drying polymorph δ, as described in EP 1698630 (2005) and that shows a twenty fold reduction of bioavailability compared to the δ form.

The different rifaximin polymorphous forms can be favourably used as homogeneous and pure products in the manufacturing of the medicinal products containing rifaximin, as the efficacy and the safety of the product can be modulated by using the right polymorphous form.

The prior art allows to understand the importance of the production conditions of the medicinal products containing rifaximin, which, in case they are not opportunely controlled, can give undesirable transformations of the rifaximin polymorphous forms.

Moreover, also working phases used in the pharmaceutical product production and involving the use of water, for example powder granulation under humid conditions, film coating process with water as solvent, drying, can modify the polymorphous form of the chosen rifaximin. Also the storage of rifaximin and of the medicinal product containing it can cause problems since humidity may modify the polymorphous form in time; thus particular attention has to be paid to manufacturing.

As previously described it is advantageous from the industrial point of view to have polymorphous forms of rifaximin under conditions independent of the environment humidity to permit the production with the water removal without modifying the polymorphism.

SUMMARY OF THE INVENTION

Disclosed herein are methods of stabilizing polymorphous forms of rifaximin comprising adding one or more polyol compounds bearing at least two hydroxy groups to a mixture comprising the polymorphous forms of rifaximin. Also disclosed are polymorphous forms of rifaximin in solid state stabilized by the methods disclosed herein. Further, disclosed herein are pharmaceutical compositions comprising rifaximin in the polymorphous β form stabilized by one or more polyols according to the methods disclosed herein. In addition, disclosed herein are methods of preparing rifaximin in polymorphous form β.

We have surprisingly found, and that is the real object of the present invention, that the addition of compounds having at least two hydroxy groups, and hereinafter referred to as polyols, give stability to the polymorphous form of rifaximin.

According to this invention, "polyols" means polyalcohols (such as ethylene glycol, propanediol, butanediol, pentanediol, erythritol, pentaerythritol, etc.); monosaccharides, disaccharides and polysaccharides, such as fructose, dextrose, sucrose, starch, cellulose and derivatives thereof (hydroxypropyl cellulose, hydroxyethyl cellulose, carboxymethyl cellulose, etc.); maltodextrin, dextrin, xanthan gum and the like; di-hydroxy acid and poly-hydroxy acids (such as malic, tartaric, citric acid, etc.). Included among polyols are those having two to seven carbon atoms and two to seven hydroxy groups.

Chemical compounds represented by the formula I are preferred:

$$H-[O-CH-(X)-CH_2]_n-OH \qquad (I)$$

where X is hydrogen or lower alkyl and n can range from 1 to 20, or 1,2,3-propanetriol and 1,2-propanediol.

In particular, when polyols are added to one of the polymorphs of rifaximin, and exactly to polymorph β, this polymorphous form does not change its crystalline form even under those conditions known until now in which these changes were observed. After drying, the water content of the polymorph β of rifaximin, disclosed in U.S. Pat. No. 7,045,620 B1, decreases to a percentage lower than 4.5%, by weight, and the polymorph is converted to polymorph α. When the polyols are added to rifaximin β, the latter is stable even when the residual water content of the solid form is lower than 4.5%; moreover the storage of this polymorph is independent of the relative ambient humidity.

Among the polymorphs of rifaximin, the β form is very important, because it is the less absorbed of all the polymorphous forms of rifaximin, as disclosed by Viscomi G. C. et al., in WO 2005/044823 (2004) and in EP 1698630 (2005). For rifaximin, a low absorption is very important, because it plays an efficacious antibacterial activity in the gastrointestinal tract versus a large spectrum of microorganisms responsible for infective diarrhoea, showing an excellent safety profile because it is not absorbed in humans, as disclosed by Dascombe J. J. et al. in Int. J. Clin. Pharmacol. Res., 1994, 14 (2), 51-56. It has been demonstrated in WO 2005/044823 and in EP 1698630 (2005) that rifaximin absorption depends only on its polymorphism and it is possible to have a difference in absorption of almost six hundred times among polymorphs; therefore the use of the polymorph β, which is the less absorbed, is very advantageous. In fact, the induction of bacterial strains resistant to the antibiotic is a possible adverse effect related to the use of antibiotics. In the case of rifaximin, this is particularly important, because rifaximin belongs to the rifampicin family, which is largely used in the treatment of tuberculosis, a pathology that had a recrudescence, as described by Kremer L. et al. in Expert Opin. Investig. Drugs, 2002, 11 (2), 153-157.

According to the present invention, among all the available polyols, those of formula H—[O—CH$_2$—CH$_2$]$_n$—OH and their mixture (where n can range between 2 and 16) as well as the compounds 1,2,3-propanetriol and 1,2-propanediol are very important, because they are all used in the preparation of pharmaceutical formulations for humans and animals, and moreover they have a plasticizing property that can make them useful as additives in pharmaceutical preparations involving coating, such as granules and tablets.

It has been found, and that is the real object of the present invention, that compounds of formula H—[O—CH$_2$—CH$_2$]$_n$—OH and their mixtures (where n can range between 2 and 16) and the compounds 1,2,3-propanetriol and 1,2-propanediol, can operate as stabilizers for the polymorphous form β and as plasticizers for the preparation of a coating that is also gastroresistant (by the use of cellulose or acrylic and methacrylic acid derivatives) and able to coat rifaximin granules and tablets, by the use of aqueous solutions of polyols at a concentration ranging between 5% (w/w) and 50% (w/w), preferably between 10% (w/w) and 30% (w/w), subsequent excess water removal and obtaining and storage of polymorphous form β.

DESCRIPTION OF THE INVENTION

As previously described, the object of the present invention is the use of polyols above described to stabilize rifaximin polymorphous forms, in particular the β form as disclosed by Viscomi G. C. et al., in U.S. Pat. No. 7,045,620B1 (2003), so as to obtain a pharmaceutical preparation containing the β form of rifaximin together with excipients well known in the state of the art, such as diluents, ligands, lubricants, disintegrants, dyes, flavors and sweeteners, wherein the residual water content of the active ingredient rifaximin is lower than 4.5% (w/w), and to maintain polymorph β unchanged during the production stage that can directly or indirectly lead to the drying of rifaximin, that is under conditions that, without the use of polyols, would not allow to conserve the β form, which would indeed be transformed into another polymorphous form of rifaximin, depending on the severity of the applied drying condition.

We found that by putting in contact rifaximin β with a polyol aqueous solution at a concentration of 5% (w/w) to 50% (w/w), and preferably between 10% (w/w) and 30% (w/w) for a period of time, generally from 1 to 24 hours, rifaximin in β form is obtained, which results stable even when the residual water content in the solid form is brought to a value lower than 4.5% (w/w).

The polyols described above or a mixture of them, which are the object of this invention, can be added to rifaximin β, either pure or mixed with a quantity of diluents known in pharmaceutical technology to improve the smoothness and to favour the interaction with polyols, or a mixture of them. For this purpose substances such as colloidal silica (for example the colloidal silica known as Aerosil®) can be used and can be added to the active ingredient in a range comprised between 1% (w/w) and 20% (w/w) and preferably between 0.2% (w/w) and 5% (w/w).

The interaction process between one of these polyols described above, or a mixture of them, and the rifaximin can be obtained by any procedure known in the pharmaceutical technology field which permits a close mixing of the components.

One of these polyols, or a mixture of them, can be applied after a suitable water dilution with a granulation process in which the solution is opportunely added to the powder containing the active ingredient, or exclusively constituted by it, with suitable mixing. The operation can be carried out in a traditional granulator or in a high speed granulator where a rotary blade and a breaker are present to favour the mixing of the components.

The addition of the solution of one or more polyols to the powder mixture can be done manually, taking care to slowly add the solution to the powder or to the powder mixture to favour the component interaction; or more opportunely, it can be carried out by a suitable pumping system; for example lobs pump, piston pump or peristaltic pump, and by the use of an atomizer allowing the nebulisation of the solution, thus favouring a better component interaction.

When the granulation is effected, the excess water can be eliminated using a traditional drying system known in the pharmaceutical technology field by drying in static oven or by drying in a fluid bed apparatus. The drying temperature can range between 30° C. and 90° C., preferably between 40° C.

and 80° C. The drying time depends on the apparatus used, on the amount of powder to be dried and on the desired residual humidity.

The application of the solution containing one of the above mentioned polyols, or a mixture of them, can be carried out also with a fluid bed apparatus. In this case, the powder containing the active ingredient, or exclusively constituted by it, is maintained in suspension by a warm air flux and at the same time the solution containing one of the above mentioned polyols or a mixture of them, is finely nebulised on the powder. In this case, the close mixture of the solution containing the polyols, or a mixture of them, with solid rifaximin, occurs at the same moment as the drying process.

The person skilled in pharmaceutical technology is able to obtain a product with the desired residual water content by changing the critical parameters, such as air inlet temperature, air inlet capacity and application velocity of the solution. Air inlet temperature is generally set between 20° C. and 90° C. and preferably between 30° C. and 80° C.

The solution application speed is closely connected to air temperature that keeps the powder under suspension. The objective, well known to the expert in the art, is to maintain the mixture temperature constant during all the process. In fact an application speed that is too fast would lead to excessive wetting, with powder agglomeration, preventing the mixture necessary to obtain an effective action on the powder; while an application speed that is too low could cause a mixture temperature increase with possible degradation of the active ingredient.

The present invention can be obtained through any other pharmaceutical process providing a close mixture of the solution containing the above mentioned polyols, or a mixture of them, and subsequent drying.

The preferred compounds having formula H—[O—$CH_2$—$CH_2$]$_n$—OH (where n can range between 2 and 10) and their mixture, and the compounds 1,2,3-propanetriol and 1,2-propanediol, can be added at concentrations comprised between 5% (w/w) and 50% (w/w), preferably between 10% (w/w) and 30% (w/w), as components of aqueous mixtures suitable for the film coating of solid oral pharmaceutical preparations, able to give a controlled release or gastro-resistance.

The invention is illustrated in the following non-limiting examples.

EXAMPLE 1

Preparation of Rifaximin β Form with Residual Water Content Lower than 4.5%

199 Grams of rifaximin β form are mixed for 5 minutes in a fluid bed apparatus having an inlet temperature of 80° C., with 1 gram of Aerosil®.

Figure 1:
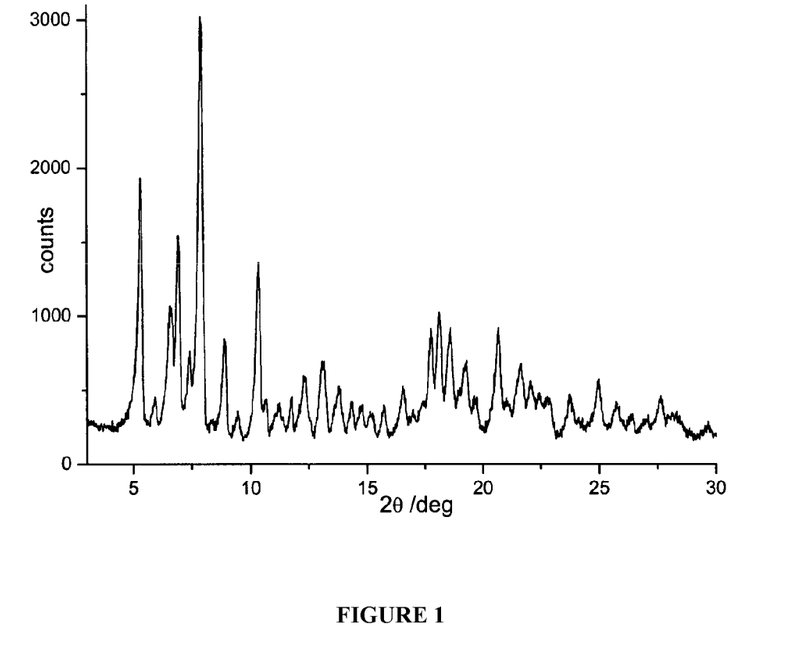
FIG. 1 is a powder X-ray diffractogram of rifaximin polymorphous form β in the presence of 1,2-propanediol.

A suspension consisting of 390 grams of water and 13 grams of 1,2-propanediol is sprayed on the mixture of rifaximin β form in a fluid bed apparatus, using a peristaltic pump with a 11 grams/minutes capacity and maintaining the temperature at a constant value of 80° C. during all the process. The mixture is dried at 80° C., and drying is continued until the weight loss is constant. The residual water content in the microgranules is determined (Karl Fisher) and it is equal to 2.2%. The microgranules thus obtained are submitted to X-ray spectroscopy and the diffractogram, which is reported in FIG. 1, corresponds to polymorph β of rifaximin which show peaks at the values of the diffraction angles 2θ of 5.3, 6.7, 7.7, 8.9, 10.4, 12.3, 17.7, 18.2, 18.6 and 20.7.

The same results are obtained when 1,2-propanediol is replaced by erythritol or mannitol.

COMPARATIVE EXAMPLE 2

This example demonstrates that in the absence of polyols, a rifaximin with a residual water content lower than 4.5% does not take the polymorphous β form, and that the polyol addition allows to obtain rifaximin in a solid state in the β form with a residual content lower than 4.5% (The operations are the same as those described in example 1, where the spayed solution does not contain 1,2-propanediol).

199 Grams of rifaximin β form are mixed for 5 minutes in a fluid bed apparatus having an inlet temperature of 80° C., with 1 gram of Aerosil®.

Figure 2:
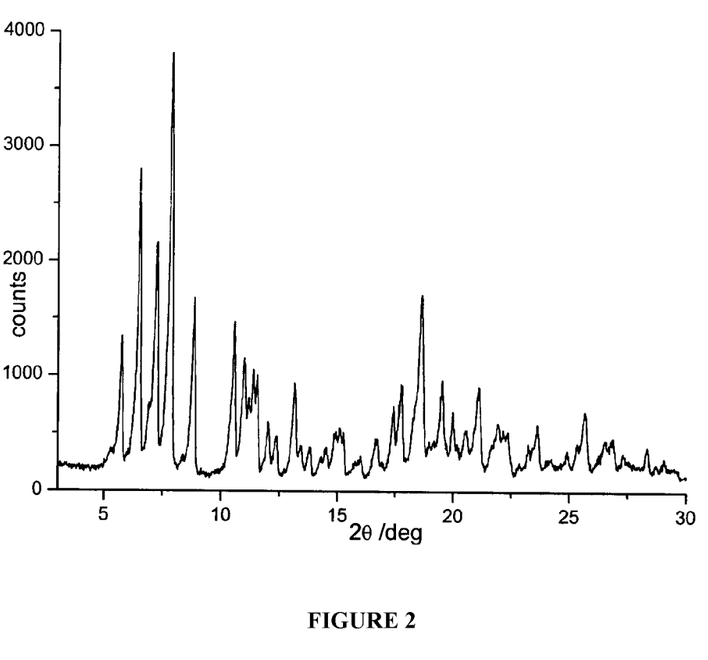
FIG. 2 is a powder X-ray diffractogram of rifaximin polymorphous form α without 1,2-propanediol.

400 Grams of water are sprayed on the mixture of rifaximin β form in a fluid bed apparatus, using a peristaltic pump with an 11 grams/minute capacity and maintaining the temperature at a constant value of 80° C. during all the process. The mixture is dried at 80° C., and drying is continued until the weight loss is constant. The residual water content in the microgranules is determined (Karl Fisher) and it is equal to 1.1%. The microgranules thus obtained are submitted to X-ray spectroscopy and the diffractogram reported in FIG. 2 corresponds to polymorph α of rifaximin.

COMPARATIVE EXAMPLE 3

This example demonstrates the importance of the presence of the hydroxy group in a polyol to obtain a rifaximin in the polymorphous β form with residual water content lower than 4.5%. The operations are the same as those described in example 1, where 1,2-propanediol is substituted by a polyol having the esterified hydroxy group, for example 1,2,3-propanetriol triacetate.

199 Grams of rifaximin are mixed for 5 minutes in a fluid bed apparatus having an inlet temperature of 80° C., with 1 gram of Aerosil®.

Figure 3:
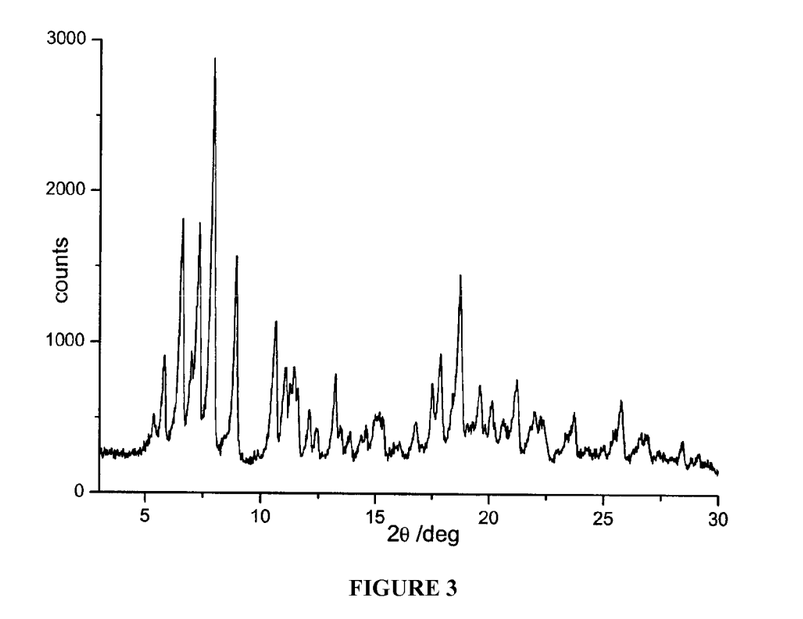
FIG. 3 is a powder X-ray diffractogram of rifaximin polymorphous form α in the presence of 1,2,3-propanetriol triacetate.

A suspension constituted by 382.75 grams of water and 12.75 grams of 1,2,3-propanetriol triacetate, is sprayed on the mixture of rifaximin in a fluid bed apparatus, using a peristaltic pump with a 11 grams/minute capacity and maintaining the temperature at a constant value of 80° C. during all the process. The mixture is dried at 80° C. and drying is continued until the weight loss is constant. The residual water content in the microgranules is determined (Karl Fisher) and it is equal to 0.5%. The microgranules thus obtained are submitted to X-ray spectroscopy and the diffractogram reported in FIG. 3 corresponds to polymorph a of rifaximin.

EXAMPLE 4

Preparation of Rifaximin β with a Residual Water Content Lower than 4.5% in the Presence of PEG 400

199 Grams of rifaximin are mixed for 5 minutes in a fluid bed apparatus having a inlet temperature of 80° C., with 1 gram of Aerosil®.

A suspension consisting of 360 grams of water and 40 grams of PEG 400 (polyethylene glycol with formula H—[O—$CH_2$—$CH_2$]$_n$—OH, is sprayed on the mixture of rifaximin in a fluid bed apparatus, using a peristaltic pump with a 6 grams/minute capacity and maintaining temperature at a constant value of 80° C. during all the process. The mixture is dried at 80° C., and drying is continued until the weight loss is constant. The residual water content in the microgranules is determined (Karl Fisher) and it is equal to 0.8%.

Figure 4:
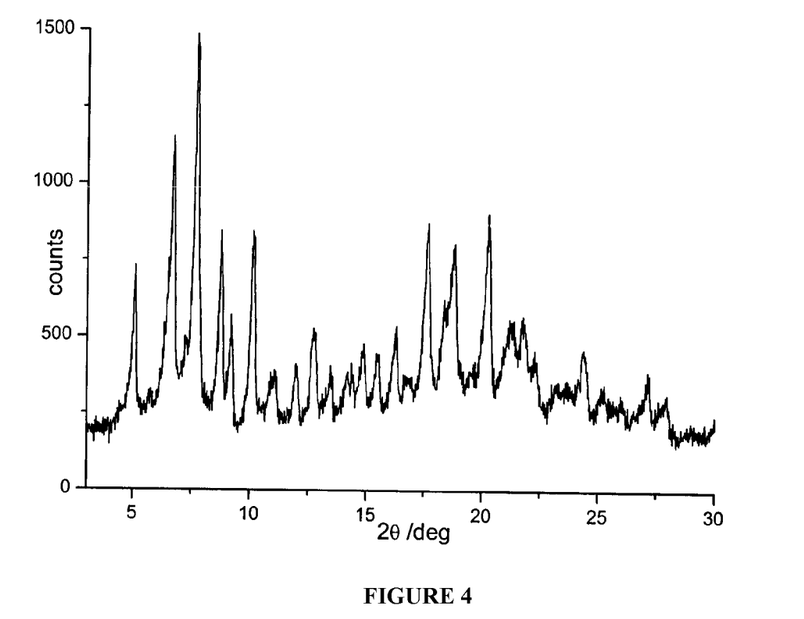
FIG. 4 is a powder X-ray diffractogram of rifaximin polymorphous form β in the presence of PEG 400.

The microgranules thus obtained are submitted to X-ray spectroscopy and the diffractogram reported in FIG. 4 corresponds to polymorph β of rifaximin. The same results are obtained using hydroxyethyl cellulose or tartaric acid instead of PEG 400.

EXAMPLE 5

Preparation of Rifaximin β Gastro Resistant Microgranules with a Residual Water Content Lower than 4.5% in the Presence of 1,2-Propanediol This example demonstrates that the polyol 1,2-propanediol added to rifaximin to obtain rifaximin β with a residual water content lower than 4.5%, can simultaneously operate as plasticizer in the preparation of films for covering granules without the addition of other compounds having this function.

25000 Grams of rifaximin powder and 125 grams of Aerosil®, that acts as a fluidiser, are loaded in a fluid bed apparatus for the application of coated films on active ingredients with film Glatt GPC 30 type, equipped with an 18 inch Wurster system.

At the same time, a suspension is prepared in a mixer under stirring as described in table 1.

TABLE 1

| Composition | Microgranules preparation |
| --- | --- |
| Demineralised water | 48107 g |
| Kollicoat ® MAE 100P | 9281 g |
| 1,2-Propanediol | 1392 g |
| Talc | 2475 g |
| Titanium dioxide FU | 557 g |
| Iron oxide E172 | 62 g |

The solid components are homogenously dispersed in demineralised water with a high speed Ultra Turrax homogenizer. The homogenized suspension is loaded in the Wurster type apparatus with a peristaltic pump and nebulised on the rifaximin powder mixture and Aerosil® 200 at a pressure comprised between 1.0 and 1.5 bar, through a 1.8 mm nozzle.

Film coating application is performed under the same conditions as described in table 2.

TABLE 2

| Process parameters | Pre-warm phase | Application of coating solution | Drying |
| --- | --- | --- | --- |
| Air flow at entrance (m³/hour) | 400 ± 100 | 550 ± 100 | 350 ± 50 |
| Air temperature at entrance (° C.) | 60 ± 2 | 60 ± 10 | 80 ± 2 |
| Product temperature (° C.) | 32 | 25-27 | 60 ± 2 |
| Jet pressure (bar) (initial phase) | | 1-1.5 ± 0.1 | |
| Jet speed (g/min) | | 150-200 | |

Residual air content on the microgranules thus obtained determined according to Karl Fischer, resulted equal to 1.2%.

Figure 5:
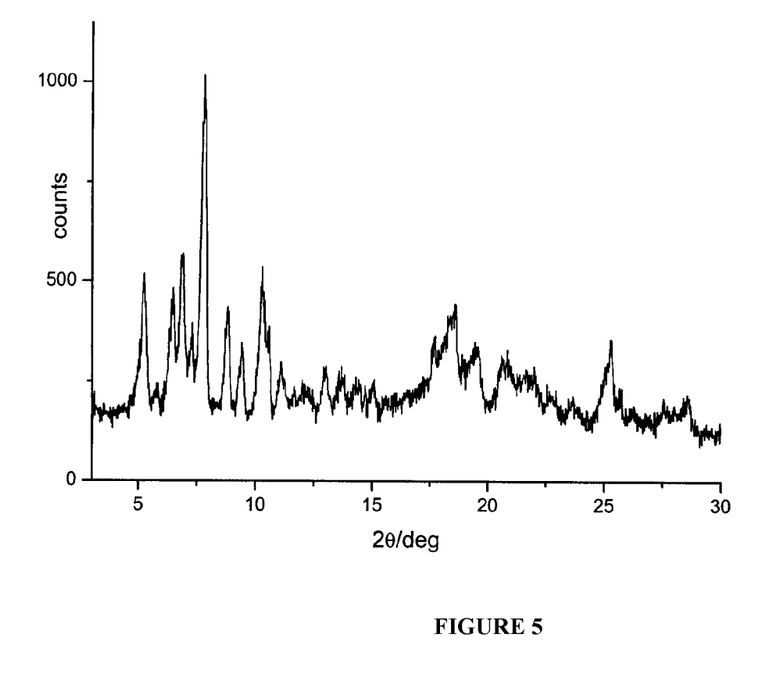
FIG. 5 is a powder X-ray diffractogram of rifaximin polymorphous β in the presence of 1,2-propanediol.

The X-ray diffractogram of the microgranules obtained, reported in FIG. 5, corresponds to polymorph β.

EXAMPLE 6

Pharmaceutical Preparation of Rifaximin β Prepared in Thermo Welded Bags 9.12 Kg of gastroresistant rifaximin microgranules prepared according to the example 5, 19.58 Kg of sorbitol, 0.49 Kg of aspartame, 0.21 Kg of anhydrous citric acid, 2.10 Kg of pectin, 2.10 Kg of mannitol, 0.21 Kg of neohesperidine DC, 1.12 Kg of cherry flavour and 0.07 Kg of silica gel are sieved on a 0.5 mm mesh sieve and then mixed for 20 minutes in a V mixer. The resulting mixture is partitioned and placed in thermo-welded bags containing 5 grams of product corresponding to 800 mg of rifaximin. The composition of the medicinal speciality contained in the thermo-welded bag is reported in the following Table 3.

TABLE 3

| | Composition of a thermo-welded bag (mg) | |
| --- | --- | --- |
| Components | (mg) | % |
| Gastroresistant rifaximin β microgranules | 1303 | 26.06 |
| Aspartame | 70 | 1.40 |
| Anhydrous citric acid | 30 | 0.60 |
| Pectin | 300 | 6.00 |
| Mannitol | 300 | 6.00 |
| Neohesperidin DC | 30 | 0.60 |
| Sorbitol | 2797 | 55.94 |
| Cherry-flavour | 160 | 3.20 |
| Silica gel | 10 | 0.20 |

Gastroresistance of microgranules contained in thermo-welded bags is evaluated after 12 months storage at 25° C. as disclosed in USP 28$^{th}$ Ed., page 2417, obtaining the same results as those obtained on the microgranules prepared as in example 1, that is a dissolution equal to 2.2% in 0.1N hydrochloric acid and equal to 91.1% in buffer at pH 6.8.

EXAMPLE 7

Pharmaceutical Preparation in the Form of Tablets Containing Rifaximin β Prepared According to Example 5

9.3 Kg of gastroresistant rifaximin microgranules prepared according to the example 1,593 g of Sodium Starch Glicolate, 100 g of magnesium stearate are sieved on a 0.5 mm mesh sieve and then mixed for 20 minutes in a V mixer. The resulting mixture is tabletted using a rotary tabletting machine (Fette 1200) equipped with oblong, scored 19×9 mm punches, yielding a final weight of 718 mg, corresponding to 400 mg of rifaximin.

The tablet composition is reported in Table 4.

TABLE 4

| | Amount | |
| --- | --- | --- |
| Tablet composition | mg | % |
| Rifaximin gastroresistant microgranules (corresponding to 400 mg of rifaximin) | 650.00 | 90.53 |
| Sodium carboxymethylcellulose | 34.95 | 4.87 |

TABLE 4-continued

| Tablet composition | Amount | |
|---|---|---|
| | mg | % |
| Avicel ® PH 101 | 24.31 | 3.34 |
| Mg-stearate | 8.74 | 1.21 |
| | 718.00 | 100.00 |

The tablets are then coated, using conventional pan equipment, with a hydroxypropylmethylcellulose film in order to improve appearance and to achieve taste-masking properties. The unitary film composition is reported in Table 5.

TABLE 5

| Coating composition | Amount (mg) |
|---|---|
| HPMC | 14.07 |
| Titanium dioxide | 4.10 |
| Na-EDTA | 0.05 |
| Propylene glycol | 1.37 |
| Red Iron Oxide E 172 | 0.41 |

The invention claimed is:

1. A method of preparing rifaximin in polymorphous form β comprising:
   i) contacting rifaximin in solid state with an aqueous solution of one or more polyols to obtain a mixture of rifaximin and polyols wherein the aqueous solution comprises one or more polyols at a concentration of 5% to 50% (w/w), and
   ii) drying the mixture of rifaximin in solid state and polyols.

2. The method of claim 1, wherein the one or more polyols are selected from the group of polyols comprising two to seven carbon atoms and two to seven hydroxy groups.

3. The method of claim 1, wherein the one or more polyols are selected from the group consisting of monosaccharides, disaccharides, polysaccharides, xanthan gum, di-hydroxy acids and poly-hydroxy acids.

4. The method of claim 1, wherein the one or more polyols are compounds of formula I:

$$\text{H---[O---CH---(X)---CH}_2]_n\text{---OH} \quad (I)$$

wherein X is hydrogen or lower alkyl, and n is between 1 and 20.

5. The method of claim 1, wherein the one or more polyols are compounds having the general formula H—[O—CH$_2$—CH$_2$]$_n$—OH, wherein n is between 2 and 14.

6. The method of claim 1, wherein the polyol is 1,2,3-propanetriol or 1,2-propanediol.

7. The method of claim 1, wherein the polyol is 1,2,3-propanetriol.

8. The method of claim 1, wherein the polyol is 1,2-propanediol.

9. The method of claim 1, wherein the contacting of said rifaximin in solid state with an aqueous solution of one or more polyols is at a temperature of between 20° C. and 90° C.

10. The method of claim 1, wherein the contacting is for a period of time of between 1 and 24 hours.

11. The method of claim 1, wherein the drying is at a temperature of between 40° C. and 80° C.

12. The method of claim 1, wherein the drying is at ambient pressure or under vacuum.

13. The method of claim 1, wherein the drying is for a period of time of between 2 and 72 hours.

14. The method of claim 1, wherein the contacting step comprises spraying the polyol aqueous solution at concentrations of from 5 to 50% (w/w) on the rifaximin β in solid state in a fluid bed apparatus having an inlet temperature of between 20° C. and 90° C., and wherein the drying step comprises drying the mixture under an air flow at a temperature of between 30° C. and 90° C.

15. The method of claim 3, wherein the polysaccharide is selected from the group consisting of starch, cellulose or derivatives thereof, dextrin and maltodextrin.

16. The method of claim 3, wherein the one or more polyols are selected from the group consisting of fructose, dextrose and sucrose.

17. The method of claim 1, wherein the polymorphous form β is characterized by peaks at the values of the diffraction angles 2θ of:
   5.3°, 7.7° and 10.4°; or
   5.3°, 7.7° and 17.7°; or
   5.3°, 7.7° and 18.2°; or
   5.3°, 10.4° and 17.7°; or
   5.3°, 10.4° and 18.2°; or
   7.7°, 10.4° and 17.7°; or
   7.7°, 10.4° and 18.2°; or
   8.9°, 17.7° and 18.2°; or
   5.3°, 7.7°, 12.3° and 17.7°; or
   5.3°, 7.7°, 12.3° and 18.2°; or
   7.7°, 12.3°, 17.7° and 18.2°; or
   5.3°, 7.7°, 12.3°, 17.7° and 18.2°; or
   5.3°, 6.7°, 7.7°, 8.9°, 10.4°, 17.7°, 18.2 and 20.7.

18. The method of claim 1, wherein the polymorphous form β is characterized by peaks at the values of the diffraction angles 2θ of 5.3, 7.7 and 18.2.

19. The method of claim 1, wherein the polymorphous form β is characterized by peaks at the values of the diffraction angles 2θ of 5.3, 6.7, 7.7, 8.9, 10.4, 12.3, 17.7, 18.2, 18.6 and 20.7.

20. A stabilized polymorphous rifaximin β in solid state obtained by the method of claim 1, wherein the polymorphous form β is characterized by peaks at the values of the diffraction angles 2θ of:
   5.3°, 7.7° and 10.4°; or
   5.3°, 7.7° and 17.7°; or
   5.3°, 7.7° and 18.2°; or
   5.3°, 10.4° and 17.7°; or
   5.3°, 10.4° and 18.2°; or
   7.7°, 10.4° and 17.7°; or
   7.7°, 10.4° and 18.2°; or
   8.9°, 17.7° and 18.2°; or
   5.3°, 7.7°, 12.3° and 17.7°; or
   5.3°, 7.7°, 12.3° and 18.2°; or
   7.7°, 12.3°, 17.7° and 18.2°; or
   5.3°, 7.7°, 12.3°, 17.7° and 18.2°; or
   5.3°, 6.7°, 7.7°, 8.9°, 10.4°, 17.7°, 18.2 and 20.7.

21. A stabilized polymorphous β form of rifaximin in solid state comprising one or more polyols wherein the polyol is selected from the group consisting of a compound having the general formula H—[O—CH$_2$—CH$_2$]$_n$—OH, wherein n is between 2 and 16.

22. The stabilized polymorphous β form of rifaximin of claim 21, wherein the one or more polyols are selected form the group consisting of 1,2,3-propanetriol, and 1,2-propanediol.

23. The stabilized polymorphous β form of rifaximin of claim 21, wherein the one or more polyols are selected from the group consisting of polyols comprising two to seven carbon atoms and two to seven hydroxy groups.

24. The stabilized polymorphous β form of rifaximin of claim 21, wherein the one or more polyols are selected from the group consisting of monosaccharides, disaccharides, polysaccharides, xanthan gum, di-hydroxy acids and poly-hydroxy acids.

25. The stabilized polymorphous β form of rifaximin of claim 24, wherein the polyols are selected from the group consisting of fructose, dextrose, sucrose, starch, cellulose and derivatives thereof, maltodextrin and dextrin.

26. The stabilized polymorphous β form of rifaximin of claim 21, wherein n is between 2 and 10.

27. The stabilized polymorphous β form of rifaximin of claim 21, wherein the polyol is 1,2,3-propanetriol.

28. The stabilized polymorphous β form of rifaximin of claim 21, wherein the polyol is 1,2-propanediol.

29. The stabilized polymorphous β form of rifaximin of claim 21, wherein the polymorphous form β is characterized by peaks at the values of the diffraction angles 2θ of:
   5.3°, 7.7° and 10.4°; or
   5.3°, 7.7° and 17.7°; or
   5.3°, 7.7° and 18.2°; or
   5.3°, 10.4° and 17.7°; or
   5.3°, 10.4° and 18.2°; or
   7.7°, 10.4° and 17.7°; or
   7.7°, 10.4° and 18.2°; or
   8.9°, 17.7° and 18.2°; or
   5.3°, 7.7°, 12.3° and 17.7°; or
   5.3°, 7.7°, 12.3° and 18.2°; or
   7.7°, 12.3°, 17.7° and 18.2°; or
   5.3°, 7.7°, 12.3°, 17.7° and 18.2°; or
   5.3°, 6.7°, 7.7°, 8.9°, 10.4°, 17.7°, 18.2 and 20.7.

30. The stabilized polymorphous β form of rifaximin of claim 21, wherein the polymorphous form β is characterized by peaks at the values of the diffraction angles 2θ of 5.3, 7.7 and 18.2.

31. The stabilized polymorphous β form of rifaximin of claim 21, wherein the polymorphous form β is characterized by peaks at the values of the diffraction angles 2θ of 5.3, 6.7, 7.7, 8.9, 10.4, 12.3, 17.7, 18.2, 18.6 and 20.7.

32. A pharmaceutical composition for the treatment of pathologies that need antibiotic therapy, said composition comprising the stabilized polymorphous β form of rifaximin of claim 24 and an excipient.

33. The pharmaceutical composition of claim 32, wherein the rifaximin is in the form of gastroresistant microgranules.

34. The pharmaceutical composition of claim 33, wherein the composition is in thermo-welded bags.

35. The pharmaceutical composition of claim 32, wherein the composition is in tablet form.

36. The pharmaceutical composition of claim 32, wherein the excipient is selected from the group consisting of diluents, ligands, lubricants, disintegrants, dyes, flavors and sweeteners.

* * * * *